United States Patent [19]

Kaetsu et al.

[11] 4,321,117

[45] Mar. 23, 1982

[54] PROCESS FOR PREPARING A POLYMER COMPOSITION

[75] Inventors: Isao Kaetsu; Masaru Yoshida; Minoru Kumakura, all of Takasaki, Japan

[73] Assignee: Japan Atomic Energy Research Institute, Tokyo, Japan

[21] Appl. No.: 18,617

[22] Filed: Mar. 8, 1979

[30] Foreign Application Priority Data

| Mar. 9, 1978 | [JP] | Japan | 53-27109 |
| Apr. 28, 1978 | [JP] | Japan | 53-51239 |
| Aug. 29, 1978 | [JP] | Japan | 53-105306 |
| Aug. 30, 1978 | [JP] | Japan | 53-106097 |

[51] Int. Cl.³ .......................... C08G 2/46; A61K 9/22
[52] U.S. Cl. ............................... 204/159.16; 128/156; 128/207.19; 128/260; 204/159.17; 204/159.22; 424/22; 424/19; 424/32; 424/33; 424/78; 424/81
[58] Field of Search ...................... 204/159.16, 159.22, 204/159.17; 424/81, 78, 22

[56] References Cited

U.S. PATENT DOCUMENTS

| 3,577,512 | 5/1971 | Shephard et al. | 424/81 |
| 3,767,790 | 10/1973 | Guttag | 424/81 |
| 3,900,559 | 8/1975 | Sim et al. | 424/22 |
| 3,901,966 | 8/1975 | Sim et al. | 424/81 |
| 3,901,967 | 8/1975 | Cohen et al. | 424/22 |
| 3,901,968 | 8/1975 | Cohen et al. | 424/22 |
| 4,025,391 | 5/1977 | Kawashima et al. | 204/159.22 |

*Primary Examiner*—Wilbert J. Briggs, Sr.
*Attorney, Agent, or Firm*—Oblon, Fisher, Spivak, McClelland & Maier

[57] ABSTRACT

A polymer composition containing a physiologically active substance which can be released at a controlled rate is prepared by contacting one or more polymerizable monomers with the physiologically active substance, mking the monomers into a specific shape and then irradiating the shaped article with light or an ionizing radiation at a low temperature below room temperature to polymerize the polymerizable monomers.

12 Claims, No Drawings

PROCESS FOR PREPARING A POLYMER COMPOSITION

BACKGROUND OF THE INVENTION

The present invention relates to a process for preparing a polymer composition containing a physiologically active substance. More particularly, the present invention relates to a process for preparing a polymer composition containing a physiologically active substance and having the property of releasing the active substance at the controlled rate.

In one aspect, the present invention relates to a process for preparing a polymer composition containing a physiologically active substance and having the property of eluting the active substance at the rate controlled by pH.

In another aspect, the present invention relates to a process for preparing a polymer composition comprising a spherical polymer matrix of 50 to 5,000μ in size containing a physiologically active substance and having the property of releasing the active substance at the controlled rate.

Various compounds having physiological activities have been broadly utilized in various fields including medical science, agriculture and engineering, and these compounds have proved to be indispensable in industry and living in many ways. Many physiologically active substances, without distinction of inorganic substance and organic substance, or low molecular compound and high molecular compound, have been known and even now are being developed. However, in the utilization of these active substances, some common defects and inconveniences have been found. One of them is a fact that in general these physiologically active subtances are effective only within a certain range of concentration in an environment in which they act, but they are not only ineffective in an concentration below such appropriate range but also often bring about harmful side reactions or side effects when they exceed the concentration range. However, on the other hand, in order to keep such organic substances continuously within the appropriate concentration range, they must be continuously replenished at an appropriate rate because they are consumed or spent simultaneously with fulfilling their function. Although there is a method of supplying or replenishing the desired substance continuously at an appropriate rate by using an apparatus or machine, the most convenient method which can be carried out in any environment and in any place is such a method that sufficient amount of the desired substance is previously contained in a certain supporting carrier so that the substance is naturally released from the carrier at the desired rate depending on the structure and function or carrier. Second, many physiologically active substances are easy to suffer a change such as deterioration and decomposition caused by various factors in an environment in which they are maintained or act, before their function is fulfilled. Therefore, it is necessary to maintain these active substances in a protected stable state until their desired function is displayed and, in this sense, it is desirable for efficiently utilizing the active substances to stabilize them by maintaining in an appropriate supporting carrier.

Mainly, for the reason as described above, such a method as containing or adsorbing various physiologically active substances in or onto an appropriate supporting carrier for use has recently come to be studied extensively. A high polymer is one of the most desirable materials as such supporting carrier. The reason is that the high polymer is a high molecular weight compound in which the desired physiologically active substances can be easily caught and maintained within the molecular structure of the compound, that the releasing rate of the desired substance can be easily controlled by adjusting the structure and shape of the polymer by means of the polymer chemical technique, and that in many cases the high polymer is physiologically neutral as a carrier so that it has no physiological effects on environment.

Therefore, the problem is now how to include or support the desired substance in a high polymer carrier in such a state that the substance can be easily released at the desired rate as described above with the original properties being not harmed.

Heretofore, high polymer materials used as a pharmaceutical additive are generally a polymer such as, for example polyvinyl alcohol, polyvinyl pyrrolidone, polyvinyl acetate, methyl cellulose, methacrylate-methacrylic acid-methyl methacrylate copolymer, methylacrylatemethacrylic acid copolymer and styrene-maleic acid copolymer. In case of mixing these polymers and medicine to form a tablet, etc., a large amount of organic solvent is required for dissolving the polymer. Such organic solvent includes chloroform-ethanol, methanol-ethylacetate, cyclohexane, acetone, ethanol, water, etc. However, these organic solvents other than ethanol and water will remain as a trace within the matrix even if the degassing treatment is apparently sufficiently carried out. In case of continuous administration of medicine over a long period, the side effect due to the cumulative build-up thereof becomes a problem. Alternatively, in case of preparing preparations which release gradually an effective ingredient contained therein (hereinafter referred to "a controlled releasing agent") in a form of tablet, film, particle, powder etc. by mixing a polymerizable monomer, a catalyst for polymerization of monomer and medicine, the following defects are noted:

(1) The reaction temperature must be raised to near 80° C. for polymerizing the monomer, and consequently the distribution state of medicine in the interior of matrix becomes not uniform and the medicine is deteriorated with high temperature;

(2) The catalyst remaining in the interior of the matrix cannot be thoroughly removed; and (3) The cost is high because it takes a few days to complete the reaction.

For example, in a case, it takes 3 days to prepare a controlled releasing agent by polymerizing 2-hydroxyethyl methacrylate and ethylene glycol dimethacrylate containing norethandrolene in the presence of t-butylperoctanoate as a catalyst under a nitrogen atmosphere at 80° C. (U.S. Ser. No. 766,840). In another example, a controlled releasing agent is prepared by polymerizing a polymerizable monomer in the presence of catalyst, impregnating the polymer obtained with a solution containing a medicine to permeate it into the interior of the matrix of polymer and drying. However, in the agent so obtained the catalyst is not removed from the matrix and it is difficult to contain a large amount of medicine per unit volume of matrix depending on the hydrophilic nature of matrix. Further, in another case a controlled releasing agent is prepared by polymerising a mixture of Cab-O-Sil EH5(RTM) and 2-hydroxyethyl methacrylate, N-vinyl-2-pyrrolidone, methyl methacrylate, divinyl benzene and t-butylperoctanoate under a nitrogen atmosphere at 54° C. for 12 hours and immersing the polymer matrix obtained into a NaCl aqueous solution containing methantheline bromide to impregnate methantheline bromide in the interior of matrix (U.S. Ser. No. 395,668; 395,492; 395,691; 395,695). However, this process comprises two steps of polymerization and impregnation of medicine, and so it is expensive.

As a result of studying on these points the present inventors have come to the following conclusion:

(1) Since many physiologically active substances have a physiological activity owing to their peculiar molecular structure, it is not desirable to expose them to such a state as being contacted with other chemicals at comparatively elevated temperatures. In this regard, it is considered to be advantageous to contain them in a high polymer carrier at a lower temperature as far as possible;

(2) In order to adjust the structure of carrier so that the desired substance is contained in the carrier sufficiently uniformly and released therefrom at an appropriate rate, the method of mixing a high polymer carrier in a monomeric state before polymerization with the desired substance and polymerizing the mixture to contain the desired substance into the carrier is excellent; and (3) It is necessary to impart the polymer such an internal porous structure or a structure having broad surface area that the desired substance can be appropriately released, and it is advantageous to design a structure and shape of polymer starting from the monomer.

The present invention has been accomplished on the basis of the principle and facts as described above.

SUMMARY OF THE INVENTION

According to the present invention, a polymerizable monomer and a physiologically active substance are mixed or contacted in the following manner:

(1) A polymerizable monomer and a physiologically active substance and/or a non-polymerizable compound (i.e. crystallizable compound) which is insoluble or soluble in the monomer and freezes at low temperatures to be crystallized or is a crystal at room temperature are mixed to prepare a solution or suspension;

(2) A polymerizable monomer and a physiologically active substance are mixed, and the mixture is added to a medium insoluble in the polymerizable monomer with or without adding an appropriate medium to prepare a microsphere comprising the polymerizable monomer and the physiological active substance, which is then separated from the medium; and (3) A polymerizable monomer is cast to a film and a physiologically active substance or a polymerizable monomer containing it and an insoluble medium are flowed on the surface thereof to prepare a monomer film having dispersed physiologically active substance on the surface.

Subsequently, the mixture of monomer and physiologically active substance prepared by any of these methods or the mixture containing a crystallizable medium is exposed to light or an ionizing radiation while cooling at low temperatures or maintaining at room temperature without heating to polymerize the polymerizable monomer in the mixture to prepare a polymer composition containing the physiologically active substance in the interior or on the surface of the polymer and having the property of releasing the active substance at a controlled rate.

In one modification of the present invention, one or more polymerizable monomers and a physiologically active substance are mixed in the presence or absence of a crystallizable substance, an adsorbent is added, and, after making to an appropriate form, the mixture is irradiated with light or an ionizing radiation at a temperature below room temperature to polymerize the monomer to prepare a controlled releasing agent which contains the physiologically active substance and release it at an appropriate rate. The modified process is characterized in that the controlled releasing property of physiologically active substance is controlled continuously over longer period by, using an adsorbent in addition to the polymerizable monomer, physiologically active substance and crystallizable substance.

In another modification, a physiologically active substance is dispersed or dissolved in a mixed solution obtained by dissolving a polymer or copolymer soluble in gastric or intestinal juice in a monomer polymerizable at low temperatures and mixing them uniformly, and after preparing various forms, the resulting dispersion or solution is irradiated with light or an ionizing radiation at a temperature below 0° C. to polymerize the monomer to prepare a polymer composition in which the elution rate of physiologically active substance contained is controlled by pH.

Further, in another modification, a mixture of one or more monomers polymerizable at a temperature below 0° C. containing a high molecular weight substance and physiologically active substances is dropped or injected into a medium at low temperatures to prepare a form of spherical structure, and thereafter is irradiated with light or an ionizing radiation to polymerize the monomers to prepare a polymer composition having the property of releasing the physiologically active substances at a controlled rate.

DETAILED DESCRIPTION OF PREFERRED EMBODIMENTS

Polymerizable monomers suitable for use in the present invention include all of various vinyl compounds, preferably ethylene dimethacrylate, diethylene glycol dimethacrylate, diethylene glycol diacrylate, triethylene glycol dimethacrylate, triethylene glycol diacrylate, tetraethylene glycol dimethacrylate, tetraethylene glycol diacrylate, polyethylene glycol dimethacrylate, polyethylene glycol diacrylate, diethylaminoethyl methacrylate, glycidyl methacrylate, epoxyacrylate, glycidyl acrylate, 2-hydroxyethyl methacrylate, hydroxyethyl acrylate, hydroxypropyl methacrylate, hydroxypropyl acrylate, hydroxybutyl methacrylate, hydroxybutyl acrylate, hydroxyhexyl methacrylate, hydroxyhexyl acrylate, butane diol dimethacrylate, butane diol diacrylate, propane diol dimethacrylate, propane diol diacrylate, pentane diol dimethacrylate, pentane diol diacrylate, hexane diol dimethacrylate, hexane diol diacrylate, neopentyl glycol dimethacrylate, neopentyl glycol diacrylate, trimethylolpropane triacrylate, trimethylolpropane trimethacrylate, trimethylolethane triacrylate, trimethylolethane trimethacrylate, polypropylene glycol diacrylate, polypropylene glycol dimethacrylate, glycerol monomethacrylate, unsaturated polyester, etc. These compounds are monomers having the property of rapidly polymerizing by light or an ionizing radiation at low temperatures, which are not crystallized at low temperatures but easily form a stable supercooled state or glass state, and which have properties preferable as a medium or carrier for supporting the desired physiologically active substance in an appropriate structure.

However, in the present invention, in addition to the above described monomers, also the following polymerizable monomers which are capable of forming a polymer singly or together with the above described monomers by irradiation can be employed: acrylic acid, methacrylic acid, N-vinyl-2-pyrrolidone, acrylamide, methacrylamide, vinyl acetate, vinyl propionate, vinyl acetate, styrene, vinyl toluene, divinyl benzene, methyl methacrylate, ethyl methacrylate, propyl methacrylate, butyl methacrylate, pentyl methacrylate, hexyl methacrylate, octyl methacrylate, lauryl methacrylate, benzyl methacrylate, cyclohexyl methacrylate, stearyl methacrylate, methyl acrylate, butyl acrylate, ethyl acrylate, maleic acid anhydride, etc.

Crystallizable ingredients contained in the polymer in the presence of polymerizable monomer in the present invention include water, dioxane, ethylene glycol, polyethylene glycol, cyclohexane, benzene, acetic acid, propionic acid, butyric acid, urea, crotonic acid, maleic acid, malic acid, succinic acid, sorbic acid, itaconic acid, n-decane, n-menane, n-hexane, n-heptane, paraffin, stearic acid, palmitic acid, lauryl alcohol, octyl alcohol, caprylic acid, caproic acid, capric acid, stearyl alcohol, palmityl alcohol, butyl stearate, methyl stearate, methyl acetate, ethyl acetate, butyl acetate, propyl acetate, propionamide, etc.

Physiologically active substances which can be used in the present invention include acetylchloline, noradrenalin, serotonin, callicrein, gastrin, secretin, adrenalin, insulin, glucagon, ACTH, growth hormone, genadotropic hormone, oxytocin, vasopressin, thyroxin, testicular hormone (teststerone), ovarian hormone (estradiol), corpus luteum hormone, luteal hormone (progesterone), adrenocortical hormone, prostagladin, various antihistaminic agents, antihypertensives, vasodilators, vasoprotectors, stomachics and digestives, anti-diarrheals and intestinal absorber, contraceptives, antiseptics and disinfectants for derma, agents for dermatozoonosis, antiphlogistic, acetysalicylic acid, ibuprofen, phenacetin, mefenamic acid, maproxen, tiaramide, indomethacin, vitamins, various enzymes, antitumor agents (bleomycin, sarcomycin, actinomycin D, cyclophosphamide, nitrogen mustard, triethylene thiophosphoramide, mercaptopurine, methotrexate, 5-fluorouracil, mitomycin C, carzinophilin, chromomycin $A_3$, 1-2(2-tetrahydro-furyl)-5-fluorouracil etc.), radiopharmaceuticals, antibiotics (streptomycins, chloramphenicols, tetracyclines, erythromycins, trichomycins, bacitracins, colistins, polymixins, gramicidins, penicillins, griseofulvins, etc.), sulfanilamide and its derivatives, antituberculosis drugs (TB preparations), antisyphilitics, antilep, various biological preparations (vaccines, antiserums, toxins and antitoxins, etc.), amebicides, anthelmintics, ataraxics, ophthalmological preparations (anticataract agents, antiglancoma agents, etc.), various fish drugs, agricultural drugs, interferon, auxin, gibberelline, cytokinin, absinthic acid, other phytohormones, sex pheromone, aggregation pheromone, alarm pheromone, trail pheromone, cast pheromone, other pheromones, various natural insecticidal substances (pyrethroid, rotinoid, nicotinoid, etc.), attractant, repellent, etc.

According to the present invention, (1) three components of physiologically active substance, polymerizable monomer and crystallizable substance as described above are mixed to prepare a solution or suspension; (2) a mixture of physiologically active substance and polymerizable monomer or the mixture added with a high molecular weight substance soluble in the monomer is dropped into a medium insoluble in the monomer to prepare a microsphere; or (3) a physiologically active substance or its solution or suspension is added onto the surface of polymerizable monomer film-cast to prepare a film of liquid mixture, and then the solution or suspension, the microsphere or the film so obtained is irradiated with light or an ionizing radiation at room temperature or a lower temperature to polymerize the monomer to prepare a polymer composition containing the physiologically active substance in the interior or on the surface of the polymer and having the property of gradually releasing the active substance at a controlled rate.

In the present invention the light includes visible and ultraviolet rays from low and high pressure mercury arc lamps, light from photon factory, natural light condensed and controlled in its intensity, and light from xenon lamp, infrared lamp, etc. And the ionizing radiation includes radiations from electron accelerator, isotope, etc., for example $\alpha$-ray, $\beta$-ray, electron beam, $\gamma$-ray, x-ray, etc. The temperature at the time of irradiating with these lights or radiation is appropriately selected from the range of from room temperature, i.e. about 30° C. to $-200°$ C., preferably 0° C. to $-100°$ C., more preferably $-20°$ C. to $-80°$ C. The reason is that even a physiologically active substance which is unstable for heat and organic chemicals and easily deprived of activity is comparatively stable in the domain of low temperature without bringing about any chemical change and is easy to handle, and that at low temperatures a crystallizable component in the mixture is crystallized and polymerized to form porosities which increase the surface area for elution of physiologically active substance and thereby the releasing rate of the desired substance can be easily controlled by adjusting the crystallizable component. And another advantage of low temperature is that most monomers used in the present invention become supercooled at low temperatures to be remarkably increased in viscosity and thereby the retention of physiologically active substance becomes secure so that the active substance is effectively contained in the polymer without being scattered and lost. Generally a method of using light or an ionizing radiation is effective for the polymerization reaction in such low temperature, but with other means it is difficult to carry out a polymerization effectively to contain the desired substance in the polymer. And, in general, when a polymer is directly added to the physiologically active substance and mixed therewith, it is necessary to heat the polymer at elevated temperatures to soften it, however, such heating at elevated temperatures is not proper since the physiologically active substance is in danger of being deteriorated and decomposed. And also there is such a method as dissolving a polymer in a solvent and then, after dissolving or dispersing a physiologically active substance in the resulting polymer solution, removing the solvent by vaporization and the like, however, it is complicated in operation to use and remove a large amount of solvent and it requires many hours and is accompanied by danger of contaminating the surroundings, and thus this method is not preferable. Furthermore, in order to maintain the desired substance in a carrier by the crosslinking structure of polymer and to control the releasing rate by changing the diffusion property in the carrier, it is often necessary to use such a polymer as having a crosslinking structure and being easily dissolved in a solvent as a material for carrier. From such points the process of the present invention is considered to be advantageous, in which the desired substance is contained by the polymerization of monomer. And then in case of mixing the desired substance and a polymer directly by kneading or mutual dissolution, such a method as growing the crystallizable component to an appropriate size of crystal for adjusting the porous structure becomes impossible, and therefore, a technique of adjusting the structure of polymer so as to be suited to the release of the desired substance is remarkably restricted.

According to the present invention, in an embodiment, one or more polymerizable monomers and physiological active substance are mixed in the presence or absence of a crystallizable substance and added with an adsorbent, and, after making to an appropriate form, the mixture is irradiated with light or an ionizing radiation to polymerize the monomer to prepare a polymer composition containing the physiologically active substance and having the property of releasing it at a controlled rate. In this case, the adsorbent added includes gelatin, agar, collagen, active carbon, silica-gel, kaolin, ion exchange resins, synthetic fiber, foamed plastic etc. And an adsorbent such as gelatin, agar, collagen, etc. is considered to control the elution of physiologically active substance by the swelling action thereof while active carbon, silica-gel, kaolin, ion exchange resins, etc. are considered to control the elution rate while partially adsorbing the solution of physiologically active substance dissolved when the elution medium permeates into the composition. By such actions, the controlled releasing property can be controlled over longer period than in case the adsorbent is not present, by 5 to 10 times or more. In the preparation of the polymer composition in this case, for 1 to 10 parts, by weight, of polymerizable monomer, 1 to 10 parts, by weight, of physiologically active substance, 1 to 5 parts, by weight, of crystallizable substance and 1 to 30 parts, by weight, of adsorbent may be used. However, these composition ratios vary with the molecular weight of polymerizable monomer, but the crystallizable substance is necessary to be completely dissolved in the polymerizable monomer.

In another embodiment, a physiologically active substance is dispersed or dissolved in a mixed solution obtained by dissolving a polymer or copolymer soluble in gastric or intestinal juice in a monomer polymerizable at low temperatures and mixing it uniformly, and, after preparing various forms of preparations, the resulting dispersion or solution is irradiated with light or an ionizing radiation at a low temperature below 0° C. to polymerize the monomer to prepare a polymer composition in which the elution rate of physiologically active substance contained is controlled by pH. The elution rate of physiologically active substance in the preparations prepared using a polymer or copolymer soluble in acid according to the present invention is recognized to be remarkable in gastric juice (pH 1 to 4) but is restrained in intestinal juice (pH 5 to 8), while, in case the polymer or copolymer component used is soluble in intestinal juice, the elution is restrained in gastric juice but is remarkable in intestinal juice. The polymer obtained by polymerizing the monomer component is a nondisintegration type of polymer which is not dissolved in gastric juice and intestinal juice. Therefore, when the polymer or copolymer component is eluted from the preparations prepared according to the present invention to gastric juice or intestinal juice, a porous structure is formed in the eluted place, and the physiologically active substance is released appropriately therefrom. The amount of polymer or copolymer component used in the preparation of the polymer composition according to the present invention is preferably 5 to 60% based on the weight of monomer component. In case of above 60%, the polymer component is not dissolved in the monomer component, and in case of 40 to 60%, all of polymer component is not completely dissolved in the monomer component. And in case of below 5%, the object intended in the present invention cannot be attained. Therefore, the most preferable amount of polymer component is 5 to 40% based on the weight of the monomer component. However, these composition ratios vary with the molecular weight of the polymer component. The physiologically active substance is used in an amount of 0.1 to 10 parts, by weight, per 10 parts, by weight, of clear uniform mixed solution of the polymer component and the monomer component.

In the preparations prepared according to this process, in case the physiologically active substance used is absorbed in stomach, the radical absorption and the inflammation of the stomach caused by the contact of a large amount of physiologically active substance with the wall of the stomach can be suppressed and the absorbing rate can be controlled. And, in case of using a physiologically active substance which is mainly absorbed in an intestinal portion, the absorption in stomach is undesirable and becomes a cause of inflammation. Thus, the physiologically active substance can be controlled by retarding the elution at the pH of gastric juice as much as possible and increasing the dissolution and elution in an intestinal portion over a long period so that the number of times of administration can be decreased.

As the polymer component used in this process, "EUDRAGIT ®E" is given as an example which is soluble in an aqueous solution of 1 to 4 in pH and "EUDRAGIT ®L" and "EUDRAGIT ®S" (made by Röhm Pharma GMBH, West Germany), and "MPM-05" and "MPM-06" (made by Tanabe Pharmaceutical Co., Japan) are given as examples which are soluble in an aqueous solution of 5 to 8 in pH. However, in addition, any other polymer or copolymer in which the solubility varies with pH in an aqueous solution may be used. Incidentally, "EUDRAGIT E" is a cation type of polymer synthesized from dimethylaminoethyl methacrylate and any other neutral methacrylic acid ester. "EUDRAGIT L" and "EUDRAGIT S" are an anion type of polymer synthesized from methacrylic acid and methacrylic acid ester. And "MPM-05" is methyl acrylate-methacrylic acid copolymer and "MPM-06" is methyl acrylate-methacrylic acid-methyl methacrylate copolymer. These polymer components must be completely soluble in the polymerizable monomer component.

Moreover, as the result of further research, it has been proved that physiologically active substances including medicines are scarcely decomposed by treating at a low temperature below 0° C. and their effect as a medicine is not lowered at all, although these substances have hitherto been considered to be easily decomposed by the irradiation of radiation. The present inventors have prepared on trial a polymer matrix having controlled releasing property by polymerizing a polymerizable monomer which is vitrificable at low temperatures in the presence of physiologically active substance at a low temperature below 0° C., and have found that the irradiation of radiation is the only means for polymerizing such vitrifiable monomer at a low temperature below 0° C., that γ-ray source ($^{60}$Co) is preferable as a radiation source though α-ray, β-ray, electron beam, neutron beam, etc. may be used, and further that it is difficult even at a lower temperature as −78° C. to form a spherical polymer with the low temperature vitrifiable monomer only. Herein, the term "low temperature vitrifiable monomer" (hereinafter abbreviated to "vitrifiable monomer") means a monomer which is not crystallized at a temperature below 0° C. but becomes supercooled state and has the maximum initial polymerization rate within the polymerization temperature domain below 0° C. near a temperature higher than the glass transition temperature by 50° C., and includes hydroxyethyl methacrylate, hydroxyethyl acrylate, hydroxypropyl methacrylate, hydroxypropyl acrylate, hydroxybutyl methacrylate, hydroxybutyl acrylate, glycol dimethacrylate, triethylene glycol dimethacrylate, polyethylene glycol #200 dimethacrylate, polyethylene glycol #400 dimethacrylate, polyethylene glycol #600 dimethacrylate, diethylene glycol diacrylate, diethylene glycol dimethacrylate, triethylene glycol diacrylate, polyethylene glycol #200 diacrylate, polyethylene glycol #400 diacrylate, polyethylene glycol #600 diacrylate, trimethylol propane trimethacrylate, trimethylol ethane trimethacrylate, trimethylol propane triacrylate, trimethylol ethane triacrylate, glycidyl methacrylate, etc. The vitrification effect appears at 0° C. and is remarkable at a temperature below −20° C., but below −100° C. the polymerization velocity is remarkably lowered.

Since these vitrifiable monomers are a supercooled liquid (highly viscous) at a temperature higher than the glass transition temperature (Tg), they turn back to the initial supercooled liquid with the lapse of time even if they once change into a sphere. At a temperature below Tg the spherical monomer is almost impossible to polymerize although it can maintain its spherical shape and thereby a spherical polymer cannot be prepared from the monomer. Then, the present inventors, as the result of further research, have found a fact that when a liquid prepared by adding an alkyl methacrylate polymer (hereinafter referred to AMA polymer) crystallizable at a temperature below 0° C. in a vitrifiable monomer and uniformly mixing them is added dropwise into a solvent cooled to a low temperature as −78° C., a stable spherical particle of vitrifiable monomer, the surface of which is coated with AMA polymer can be obtained, and, on the basis of the fact, have accomplished a process for preparing a polymer composition having the property of releasing a physiologically active substance at a controlled rate which comprises dropping or injecting a mixture of one or more vitrifiable monomers containing 5 to 50%, by weight, of natural or synthetic high molecular weight substance and physiologically active substance into a medium at low temperatures to form a spherical structure of 10 to 5,000μ in size and then irradiating it with light or an ionizing radiation at a temperature below room temperature to polymerize the vitrifiable monomer, and a process for preparing a polymer composition comprising a spherical matrix of 50 to 5,000μ in size having the property of releasing a physiologically active substance at a controlled rate which comprises dispersing 0.001 to 10 part, by weight, of physiologically active substance to 10 parts, by weight, of vitrifiable monomer containing 5 to 35%, by weight, of AMA polymer to uniformly disperse the active substance in the monomer, dropping or injecting the resulting dispersion into a medium cooled to −40° to −100° C. through a nozzle of 0.1 to 4 mm and then irradiating it with γ-ray from $^{60}$Co or $^{127}$Cs, or β-ray from $^{90}$Sr or electron beam from accelerator to polymerize the vitrifiable monomer and thereafter removing the solvent and drying.

In the present invention, the spherical particles do not adhere to each other after the polymerization since they are completely coated with AMA polymer. The dropping into a coolant may be carried out at atmospheric pressure or under pressure, and also may be accompanied by stirring. In addition of dropping method, any method including injection method, which is capable of making a droplet to be spherical, may be employed.

Natural or synthetic high molecular weight substances used in this process include polystyrene, vinyl acetate resin, polymethyl methacrylate, polyvinyl pyrrolidone, styrene-methyl methacrylate copolymer, methyl acrylatemethacrylate acid copolymer, 2-methyl-5-vinylpyridine-methyl acrylate-methacrylic acid copolymer, methyl acrylatemethacrylic acid-methyl methacrylate copolymer, polyvinylalcohol, acetic acid cellulose phthalate, cellulose acetate, dimethylaminoethyl methacrylate-methyl methacrylate copolymer styrene-maleic acid copolymer, hydroxypropyl cellulose, hydroxypropylmethyl cellulose, hydroxyethylmethyl cellulose, hydroxypropylmethyl cellulose phthalate, methyl cellulose etc.

The coolant used in this process includes alcohols, alkyl cellosolves, p-dioxan, etc. and is not particularly limited if it is liquid at the time of making a sphere and polymerization, however, considering a possibility that it may remain in the polymer matrix, ethyl alcohol is particularly preferable for animals, especially a human being.

The present invention will be more in detail illustrated with the following examples.

EXAMPLES 1 to 6

600 mg of potassium chloride, polymerizable monomer comprising 2-hydroxyethyl methacrylate (shown as "HEMA" in Table 1) and diethylene glycol dimethacrylate (shown as "DGDA" in Table 1) in any composition and polyethylene glycol #600 were mixed in a glass ampule of 14 mm in inner diameter and cooled to a dry ice-methanol temperature of −78° C. and thereafter irradiated with γ-ray from $^{60}$Co with a dose rate of $5 \times 10^5$ R/hr at the same temperature for 2 hours to obtain a composite tablet. The elution of potassium chloride from the composite obtained was conducted in distilled water of 6.1 in pH at 100 r.p.m. agitation in the manner described in U.S.P. XIX. The elution property of potassium chloride, composition of polymerizable monomer and amount of polyethylene glycol #600 added were shown in Table 1.

TABLE 1

| | Composition | | Amount of potassium chloride eluted (%) | |
|---|---|---|---|---|
| Example | Composition of polymerizable monomer (%) and amount added | Amount of polyethylene glycol #600 added | 3 hours after start of test | 6 hours after start of test |
| 1 | 100% HEMA; 0.6 ml | — | 45 | 65 |

TABLE 1-continued

| Example | Composition of polymerizable monomer (%) and amount added | Amount of polyethylene glycol #600 added | Amount of potassium chloride eluted (%) 3 hours after start of test | Amount of potassium chloride eluted (%) 6 hours after start of test |
| --- | --- | --- | --- | --- |
| 2 | 100% DGDA; 0.5 ml | — | 8 | 15 |
| 3 | 100% DGDA; 0.15 ml | 0.35 ml | 30 | 50 |
| 4 | 100% HEMA; 0.40 ml | 0.10 ml | 62 | 89 |
| 5 | 70% HEMA- 30% DGDA; 0.5 ml | — | 27 | 46 |
| 6 | 70% HEMA- 30% DGDA; 0.25 ml | 0.25 ml | 42 | 60 |

EXAMPLE 7

3 g of bleomycin hydrochloride were uniformly dispersed in a precopolymer sline obtained by previously irradiating a polymerizable monomer comprising 95 parts, by weight, of diethylaminoethyl methacrylate and 0.5 parts, by weight, of trimethylolpropane trimethacrylate with γ-ray from $^{60}$Co with a dose rate of $1 \times 10^6$ R/hr for 1 hour. The prepolymer was made into a film of 50 to 400 μm in thickness using a casting apparatus made of glass plate and thereafter irradiated with γ-ray from $^{60}$Co with a dose rate of $5 \times 10^5$ R/hr at −60° C. for 1 hour to obtain a film containing bleomycin hydrochloride which has a wealth of flexibility.

The elution of bleomycin hydrochloride from the film obtained was conducted in distilled water of 6.1 in pH at 100 r.p.m. agitation in the manner described in U.S.P. XIX. The amount of bleomycin hydrochloride eluted was almost constant with time and after 168 hours 93% of the initial concentration was eluted.

EXAMPLE 8

An aqueous solution of 5 mg of mitomycin C dissolved in 0.10 ml of distilled water and 0.40 ml of polyethylene glycol #600 dimethacrylate containing 5% trimethylene glycol dimethacrylate were mixed. This solution was dropped into a toluene coolant cooled to −78° C. through a nozzle to prepare a particle of about 2 mm in diameter, which was then irradiated with γ-ray from $^{60}$Co with a dose rate of $1 \times 10^6$ R/hr at −78° C. for 1 hour to obtain a spherical polymer matrix.

The elution of mitomycin C from the matrices obtained was conducted in distilled water of 6.1 in pH at 100 r.p.m. agitation in the manner described in U.S.P. XIX. The amount of mitomycin C eluted was 2% in 3 hours and 57% in 6 hours after start of test and reached 94% in 12 hours.

EXAMPLE 9

500 mg of betamethason and 0.8 ml of trimethylolpropane trimethacrylate were uniformly dispersed in an ampule of 8 mm in diameter and, after cooling to −50° C., were irradiated with γ-ray from $^{60}$Co with a dose rate of $2 \times 10^5$ R/hr for 3 hours to prepare a polymer matrix containing betamethason. The polymer matrix was crushed to below 50 μm by means of a crusher and the elution of betamethason was conducted in distilled water of 6.1 in pH at 100 r.p.m. agitation in the manner described in U.S.P. XIX. The amount of betamethason eluted was constant with time and reached 92% in 48 hours after start of test.

EXAMPLE 10

1,200 mg of contraceptive, norethandrolone, and 1 ml of trimethylolpropane trimethacrylate containing 30% tetramethylolmethane tetraacrylate were uniformly dispersed in a glass ampule of 6 mm in inner diameter and, after cooling to −78° C., were irradiated with γ-ray from $^{60}$Co with a dose rate of $5 \times 10^5$ R/hr for 2 hours.

The elution rate of norethandrolone from the rod like polymer matrix was determined in purified water of 7.0 in pH at 50 r.p.m. agitation in the manner described in U.S.P. XIX. The amount of norethandrolone eluted was constant with time and reached 89% in 400 days after start of test.

EXAMPLE 11

600 mg of ibuprofen and 3 ml of ethyleneglycol dimethacrylate were uniformly dispersed in a glass ampule of 8 mm in inner diameter and, after deaerating ($10^{-4}$ to $10^{-3}$ mmHg) several times, cooled to −78° C. and irradiated with γ-ray from $^{60}$Co with a dose rate of $5 \times 10^5$ R/hr for 3 hours to prepare a polymer matrix containing ibuprofen. The polymer matrix was crushed to below 500 μm by means of a crusher and the elution of ibuprofen was conducted in the second liquid (ph 7.5) described in Japanese Pharmacopoeia IX (J.P IX) at 100 r.p.m. agitation in the same manner as described in United States Pharmacopoeia XIX (U.S.P. XIX). The amount of ibuprofen eluted was constant with time and reached 81% in 12 hours after start of test.

EXAMPLE 12

5 parts, by weight, of bleomycin hydrochloride were added to 10 parts, by weight, of diethylene glycol dimethacrylate containing 15%, by weight, of polymethyl methacrylate, and the resulting monomer solution containing bleomycin hydrochloride was added dropwise through a nozzle of 0.5 mm in inner diameter into ethanol cooled to −78° C. by dry ice-ethanol in such a way that the bleomycin hydrochloride was uniformly dispersed in the monomer liquid by stirring. Thereafter γ-ray from $^{60}$Co was irradiated thereto with a dose rate of $2 \times 10^5$ R/hr at −78° C. for 3 hours. After irradiation, it was removed ethanol and dried to obtain a hard spherical polymer matrix of 1 mm in average diameter. Unreacted monomer was not detected by gas chromatography.

When the spherical matrix was placed into 1,000 ml of distilled water at 37° C. and stirred at 100 r.p.m. to elute out bleomycin hydrochloride, the elution rate was observed to be constant during one month. The total amount of bleomycin eluted reached 90% of the initial charge.

EXAMPLE 13

3 parts, by weight, of cyclophosphamide were added to 10 parts, by weight, of 2-hydroxyethyl methacrylate containing 10%, by weight, of polymethyl methacrylate, and the resulting dispersion was dropped into ethanol cooled to −78° C. through a nozzle of 2 mm in inner diameter in such a state that the cyclophosphamide was uniformly dispersed in the monomer liquid by stirring to prepare a spherical monomer. Thereafter, the ethanol mixture containing the spherical monomer particles was irradiated with γ-ray from $^{60}Co$ with a dose rate of $8 \times 10^5$ R/hr at $-78°$ C. for 1 hour. After irradiation, ethanol was removed and dried to obtain a somewhat hard spherical polymer matrix of 3.5 mm in average diameter. Unreacted monomer was not detected by gas chromatography. The spherical polymer matrix containing cyclophosphamide was charged into 1,000 ml of distilled water at 37° C. retating at 100 r.p.m. The elution rate of cyclophosphamide from the matrix was constant during 12 hours. The total amount of cyclophosphamide eluted for 12 hours corresponded to 85% of the initial charge.

EXAMPLE 14

4 parts, by weight, of 1-2(2-tetrahydro-furyl)-5-fluorouracil were added to 10 parts, by weight, of trimethylolpropane trimethacrylate containing 15%, by weight, of polymethyl methacrylate and the resulting monomer dispersion was injected into ethanol cooled to $-78°$ C. through a nozzle of 0.15 mm in inner diameter under pressure while stirring. Thereafter, the spherical monomer in the ethanol coolant was irradiated with γ-ray from $^{60}Co$ with a dose rate of $1 \times 10^5$ R/hr at $-78°$ C. for 6 hours. After irradiation, ethanol was removed and dried to obtain a hard spherical polymer matrix of 0.3 mm in average diameter. Unreacted monomer was not detected by gas chromatography.

The spherical polymer matrix containing 1-2(2-tetrahydro-furyl)-5-fluorouracil was charged into 1,000 ml of distilled water at 37° C. rotating at 100 r.p.m. The elution rate of 1-2(2-tetrahydro-furyl)-5-fluorouracil from the matrix was constant during 2 months. The total amount eluted for 2 months reached 88% of the initial charge.

EXAMPLE 15

1 part, by weight, of betamethason was added to 10 parts, by weight, of glycidyl methacrylate containing 10%, by weight, of polystyrene and betamethason was uniformly dispersed in the monomer by stirring. And then the monomer containing betamethason was injected into a medium cooled to $-78°$ C. by dry ice and ethanol under pressure of nitrogen gas. Thereafter, the monomer in the medium was irradiated with γ-ray from $^{60}Co$ with a dose rate of $1 \times 10^6$ R/hr at $-78°$ C. for 1 hour. After irradiation, ethanol was removed and dried to obtain a hard spherical polymer matrix of 0.030 mm in average diameter. Unreacted monomer was not detected by gas chromatography. The spherical polymer matrix containing betamethason was charged into 1,000 ml of distilled water at 37° C. rotating at 100 r.p.m. The elution rate of betamethason from the matrix was constant during 3 days, and the total amount eluted reached 91% of the initial charge.

EXAMPLE 16

10 parts, by weight, of polyethylene glycol #600 were added to 10 parts, by weight, of diethylene glycol dimethacrylate containing 10%, by weight, of polyvinylalcohol, and further 1 part, by weight, of indomethacin was added thereto and uniformly dispersed in the monomer solution. The monomer solution containing indomethacin was dropped into an ethanol medium cooled to $-78°$ C. in the same manner as described in Example 12. Thereafter, it was irradiated with γ-ray from $^{60}Co$ with a dose rate of $7 \times 10^5$ R/hr at $-78°$ C. for 1 hour. After irradiation, ethanol was removed and dried to obtain a spherical polymer matrix of 2 mm in average diameter. Unreacted monomer was not detected by gas chromatography. The spherical matrix containing indomethacin was charged into 1,000 ml of distilled water at 37° C. rotating at 100 r.p.m. to check the elution property. The elution rate of indomethacin from the matrix was constant during 7 hours and the total amount eluted reached 85% of the initial charge.

EXAMPLE 17

3 parts, by weight, of bleomycin hydrochloride were added to 10 parts, by weight, of trimethylolpropane triacrylate containing 10%, by weight, of vinyl acetate polymer, and the resulting monomer solution containing bleomycin hydrochloride was dropped into ethanol cooled to $-78°$ C. by dry ice-ethanol through a nozzle of 0.4 mm in inner diameter in such a way that the bleomycin hydrochloride was uniformly dispersed in the monomer liquid. Thereafter, a light (maximum energy wave length 3,600 Å) from a high pressure mercury vapour lamp made by Toshiba Co. was irradiated thereto for 2 hours. After irradiation, ethanol was removed and the polymer was dried to obtain a hard spherical matrix of 0.9 mm in average diameter. Unreacted monomer was not detected by gas chromatography. When the spherical matrix was charged into 1,000 ml of distilled water at 37° C. and stirred at 100 r.p.m. to elute out bleomycin hydrochloride from the matrix, the elution rate was observed to be constant during 25 days. The total amount eluted reached 85% of the initial charge.

EXAMPLE 18

Example 17 was repeated except irradiating β-ray from $^{90}Sr$ with the total dose of $7 \times 10^5$ R at $-78°$ C. in place of using the high pressure mercury vapour lamp. The elution of bleomycin hydrochloride from the spherical matrix (0.9 mm) obtained was almost the same as in Example 17.

In the following Examples 18 to 24, the elution test of chemicals from the preparations obtained according to the present invention was conducted at $37 \pm 0.5°$ C. in the manner described in U.S.P. XIX while rotating a stainless steel basket at 100 r.p.m.

EXAMPLE 19

10 parts, by weight, of aspirin were added to 10 parts, by weight, of clear uniform mixed solution of 2-hydroxyethyl methacrylate containing 30%, by weight, of "EUDRAGIT ®E" in a glass ampule which was then degassed and sealed, and then was quenched to $-78°$ C. (in a dry ice-methanol coolant) in such a way that aspirin is apparently uniformly dispersed in the clear uniform mixed solution, and thereafter was irradiated with γ-ray from $^{60}Co$ with a dose rate of $5 \times 10^5$ R/hr at $-78°$ C. for 2 hours to polymerize 2-hydroxyethyl methacrylate completely to prepare a preparation. The preparation so obtained was crushed to 12 to 32 mesh and then tested by the elution test. The amount of aspirin eluted in an aqueous solution of 3.0 in pH reached 96% of the initial charge in 2 hours and the elution rate was observed to be constant.

And the amount of aspirin eluted in an aqueous solution of 7.0 in pH reached 35% of the initial charge. For comparison, the amount of aspirin eluted from a preparation prepared under the same condition except not containing "EUDRAGIT E" corresponded to 19% and 22% of the initial charge in an aqueous solution of 3.0 and 7.0, respectively, in pH.

EXAMPLE 20

8 parts, by weight, of potassium chloride were dispersed and mixed to 10 parts, by weight, of polymerizable monomer mixed solution comprising 70% of 2-hydroxyethyl methacrylate and 30% of trimethylolpropane trimethacrylate containing 25%, by weight, of "EUDRAGIT®L", and thereafter the dispersed mixed solution was poured into a vinyl chloride polymer tube of 4 mm in inner diameter and simultaneously quenched to −78° C. (in a dry ice-methanol coolant), and, in this state, was irradiated with a dose rate of $1 \times 10^6$ R/hr under a nitrogen atmosphere to copolymerize 2-hydroxyethyl methacrylate and trimethylolpropane trimethacrylate to convert them to a polymer by 100%. The resulting high polymer composition was cut to a chip of 4 mm in diameter and 4 mm in height by a cutter. When the elution test of potassium chloride from the chip was conducted in an aqueous solution of 3.0 in pH, the amount eluted for 6 hours reached 31% of the initial charge. And in an aqueous solution of 7.0 in pH the amount of potassium chloride eluted reached 94% of the initial charge after 6 hours. For comparison, the amount of potassium chloride eluted from a high polymer composition prepared under the same condition except not containing "EUDRAGIT L" corresponded to 16% of the initial charge in an aqueous solution of 3.0 in pH and to 27% in an aqueous solution of 7.0 in pH.

EXAMPLE 21

6 parts, by weight, of creosote were added and mixed to 10 parts, by weight, of hexanediol monomethacrylate containing 15%, by weight, of "MPM-06" and the resulting mixed solution was injected into a glass casting apparatus to make a film of 50μ in thickness, and, thereafter, was irradiated with electron beam from an electron beam accelerator of 2 MeV with $1 \times 10^6$ rad under a nitrogen atmosphere at −60°±5° C. to polymerize hexanediol monomethacrylate. The amount of creosote eluted from the resulting film was 9% of the initial charge for 4 hours in case of an aqueous solution of pH 3.0 and 55% in case of an aqueous solution of pH 7.0.

EXAMPLE 22

4 parts, by weight, of bleomycin hydrochloride, 10 parts, by weight, of a mixture consisting of 30% of glycidyl methacrylate and 70% of trimethylolpropane trimethacrylate and 4 parts, by weight, of silica-gel below 200 mesh were dispersed and mixed, and the resulting dispersion mixture was placed into a casting apparatus made of glass plate and irradiated with γ-ray from $^{60}$Co with a dose rate of $1 \times 10^5$ R/hr at a irradiation temperature of −70°±5° C. for 5 hours to prepare a film of 100μ in thickness.

The amount of bleomycin hydrochloride eluted from the film preparations obtained was almost constant with time and 92% of the initial charge was observed to be eluted during 150 days. For comparison, in case of a film preparation prepared under the same conditions except not coexisting silica-gel, the amount of bleomycin hydrochloride eluted was 90% of the initial charge during 25 days.

EXAMPLE 23

3 parts, by weight, of 5-fluorouracil, 5 parts, by weight, of hydroxyethyl acrylate, 2 parts, by weight, of polyethylene glycol #400 and 3 parts, by weight, of active carbon of 65 to 115 mesh were dispersed and mixed, and the resulting dispersion mixture was poured into a polyethylene tube of 5 mm in inner diameter and simultaneously was quenched to −78° C. (dry ice-methanol). Thereafter, the mixutre was irradiated with γ-ray from $^{60}$Co with a dose rate of $5 \times 10^5$ R/hr in a nitrogen atmosphere for 2 hours to convert hydroxyethyl acrylate to a polymer by 100%.

The preparation so prepared was cut to a pellet of 5 mm in diameter and 5 mm in height. And when the amount of 5-fluorouracil eluted from the preparation was determined, the elution rate was observed to be constant during 35 hours and the amount reached 95% of the initial charge. For comparison, the amount of 5-fluoro-uracil eluted from a preparation prepared under the same conditions except without active carbon was 89% for 6 hours.

EXAMPLE 24

3 parts, by weight, of progesterone, 6 parts, by weight, of a mixture consisting of 20% of diethylene glycol dimethacrylate and 80% of trimethylolpropane trimethacrylate, 2 parts, by weight, of polymethyl methacrylate and 3 parts, by weight, of Amberlyst 15 (made by Organo Co.) were dispersed and mixed, but, polymethyl methacrylate was previously dissolved in a mixed solution of ethylene glycol dimethacrylate and trimethylolpropane trimethacrylate. The resulting dispersion mixture was dropped into a ethanol coolant cooled to −78° C. to prepare a monomer capsule of 4 mm in average diameter and thereafter irradiated with γ-ray from $^{137}$Cs with a dose rate of $1 \times 10^5$ R/hr at this coolant temperature for 8 hours to prepare a polymer capsule containing progesterone. The elution rate of progesterone from the polymer capsule was constant over 13 months and the total amount reached 87% of the initial charge. For comparison, the amount of progesterone eluted from a polymer capsule prepared under the same condition except without Amberlyst 15 reached 84% for 2 months.

EXAMPLE 25

A dispersion mixture comprising 3 parts, by weight, of methyl salicylate, 3 parts, by weight, of gelatin and 6 parts, by weight, of 2-hydroxyethyl methacrylate was poured into a flat type of glass ampule and thereafter irradiated with electron beam from an electron beam accelerator of 2 MeV with $1.5 \times 10^6$ rad under a nitrogen atmosphere at −70°±5° C. The preparation obtained was crushed to 32 to 65 mesh. The elution rate of methyl salicylate from the crushed preparation was constant over 48 hours, and the total amount reached 96% of the initial charge. For comparison, the amount of methyl salicylate eluted from a preparation prepared under the same condition except without gelatin reached 90% for 3 hours.

In the process of the present invention, starting from a mixture of monomer and physiologically active substance, the composition is prepared by polymerizing it. The property of releasing the physiologically active substance from the composition can be changed and controlled to the desireed releasing rate by selecting the kinds of monomer or devising a combination and composition in plural monomers system, considering the affinity of monomer and its polymer for physiologically active substance, crystallizable component and medium in an environment in which the composition is used, and others, according to the molecular size, chemical properties, solubility, etc. of the physiologically active substance, or by adjusting the kind and amount of crystallizable component added as needed, the temperature and cooling velocity when the component is crystallized, the temperature and dose when the polymerization is effected by irradiation and other polymerization conditions.

In addition to microsphere, film, etc., the mixture of monomer and physiologically active substance can be cast into various shapes of frame or mold to form a block, fiber, tube and other shapes which are then polymerized to provide various shapes of controlled releasing composition. The polymer composition so obtained can be not only utilized in medical uses such as therapeutics, prophylactic diagnosis and inspection in a form of internal medicine, suppository, external remedy, artificial internal organs, or the like, but also can be broadly utilized in the fields of agriculture, gardening forestry, fishery, animal husbnadry, etc. in a form of fish drug, agricultural chemicals, insecticide, anthelmintic, or the like. Furthermore, the mixture can be utilized for rearing and culture of vegetation and microorganisms using a composition containing growth hormone, multiplication accelerator of microorganism, inhibitor for interrupting substance, etc., and also can be utilized for control and acceleration of reaction in food industry and medical industry using a composition containing stabilization ion for enzyme, assistant for enzyme reaction, inhibitor for interrupting substance, etc.

We claim:

1. A process for preparing a polymer composition containing a physiologically active substance characterized by contacting one or more polymerizable monomers and said physiologically active substance in the presence of a crystallizable substance, forming into a specific shape, and irradiating said shape with light or an ionizing radiation at a low temperature below room temperature to polymerize said polymerizable monomers, said crystallizable substance being crystallized at the irradiation temperature.

2. The process as set forth in claim 1 wherein the contact of polymerizable monomer and physiologically active substance is carried out by dispersing said active substance on the surface of a film of said monomer.

3. The process as set forth in claim 1 wherein said shape is a solution, suspension, microsphere or liquid film.

4. The process as set forth in claim 1 wherein the contact is carried out by mixing the polymerizable monomer and physiologically active substance in the presence of crystallizable substance and thereafter an adsorbent is added thereto and the irradiation temperature is below 0° C.

5. The process as set forth in claim 4 wherein said adsorbent is selected from gelatin, agar, collagen, active carbon, silica-gel, kaolin, and an ion-exchange resin.

6. The process as set forth in claim 1 wherein the contact is carried out by dispersing or uniformly mixing said physiologically active substance in a mixed solution comprising a polymer or copolymer soluble in a pH within the range of 1 to 10.0 and a monomer polymerizable at low temperatures and the irradiation temperature is below 0° C.

7. The process as set forth in claim 6 wherein the amount of said polymer or copolymer completely dissolved in a solution of 1 to 10.0 in pH is 5 to 60% based on the weight of said monomer.

8. The process as set forth in claim 6 wherein the amount of physiologically active substance is 0.1 to 10 parts, by weight, per 10 parts, by weight of said mixed solution.

9. The process as set forth in any one of claims 1–8 wherein said ionizing radiation is $\gamma$-ray from $^{60}$Co or $^{137}$Cs, $\beta$-ray from $^{90}$Sr or electron beam from an accelerator.

10. A process for preparing a polymer comppsition comprising a spherical matrix of 50 to 5,000$\mu$ in size having a function of releasing a physiologically active substance at a controlled rate which comprises adding 0.001 to 10 parts, by weight, of said physiologically active substnace to 10 parts, by weight, of monomer vitrifiable at low temperatures containing 5 to 35%, by weight, of polyalkyl methacrylate to uniformly disperse said active substance in said monomer, dropping or injecting the resulting dispersion into a medium cooled to $-40°\sim100°$ C. through a nozzle of 0.1 to 4 mm, and thereafter irradiating it with $\gamma$-ray from $^{60}$Co or $^{137}$Cs, or $\beta$-ray from $^{90}$Sr, or electron beam from accelerator, to polymerize said monomer.

11. A process for preparing a polymer composition having a function of releasing a physiologically active substance at a controlled rate which comprises dropping or injecting a mixture of one or more monomers vitrifiable at low temperatures containing 5 to 50%, by weight, of a polyalkyl methacrylate and said physiologically active substance into a medium at low temperatures to make it into a shape of spherical structure, and thereafter irradiating it with light or an ionizing radiation at a low temperature below room temperature to polymerize said monomers.

12. A process for preparing a polymer composition having a function of releasing a physiologically active substance at a controlled rate which comprises dropping or injecting a mixture of one or more monomers vitrifiable at low temperatures containing 5 to 50%, by weight, of polystyrene and said physiologically active substance into a medium at low temperatures to make it into a shape of spherical structure, and thereafter irradiating it with light or an ionizing radiation at a low temperature below room temperature to polymerize said monomers.

* * * * *